United States Patent [19]
Waterson et al.

[11] Patent Number: 5,137,026
[45] Date of Patent: Aug. 11, 1992

[54] PERSONAL SPIROMETER

[75] Inventors: Charles K. Waterson, Chapel Hill, N.C.; Frederick A. Ebeling, Tucson, Ariz.

[73] Assignee: Glaxo Australia Pty., Ltd., Victoria, Australia

[21] Appl. No.: 461,089

[22] Filed: Jan. 4, 1990

[51] Int. Cl.$^5$ .............................................. A61B 5/091
[52] U.S. Cl. .................................... 128/725; 73/861.52
[58] Field of Search ...................... 128/725; 73/861.42, 73/861.52, 861.61

[56] References Cited

U.S. PATENT DOCUMENTS

| | | |
|---|---|---|
| 3,433,217 | 3/1969 | Rieke . |
| 3,504,542 | 4/1970 | Blevins . |
| 3,577,984 | 5/1971 | Levy . |
| 3,606,883 | 9/1971 | Poirier et al. . |
| 3,608,546 | 9/1971 | Shinn . |
| 3,621,835 | 11/1971 | Suzuki et al. . |
| 3,626,755 | 12/1971 | Rudolph . |
| 3,635,214 | 1/1972 | Rand et al. ............................ 18/727 |
| 3,645,133 | 2/1972 | Simeth et al. . |
| 3,703,893 | 11/1972 | Hardway, Jr. . |
| 3,713,337 | 1/1973 | Stroman ........................... 73/861.42 |
| 3,720,202 | 3/1973 | Cleary ................................... 128/727 |
| 3,722,506 | 3/1973 | McMillan, Jr. . |

(List continued on next page.)

FOREIGN PATENT DOCUMENTS

| | | |
|---|---|---|
| 2941426 | 2/1981 | Fed. Rep. of Germany . |
| 3322536 | 1/1985 | Fed. Rep. of Germany . |
| WO84/1704 | 5/1984 | PCT Int'l Appl. . |
| AU 89/261 | 12/1989 | PCT Int'l Appl. . |
| 1160669 | 8/1969 | United Kingdom . |
| 1351112 | 4/1974 | United Kingdom . |
| 1463814 | 2/1977 | United Kingdom . |
| 2133157 | 7/1984 | United Kingdom . |

OTHER PUBLICATIONS

Lecky, John H. et al "A New Disposable Spirometer" Anesthesiology vol. 38, No. 5, Mar. 1973.
Melia, R. J. W. et al "Suitability of a New Turbine Spirometer" Bull. Eur. Physiopathol. Respir. vol. 21; 43–47, 1985.
Elliott, Stanley E. "Turbulent airflow meter" J. Appl. Physiol. vol. 42(3) pp. 456–460, 1977.
American Thoracic Society Statement "Standardization of Spirometry" Respiratory Care, Nov. 1987 vol. 32, No. 11 1040–1060.
Timeter's L.A.P. Spirometry System, Aug. 15, 1987 (Product Literature).
Chowienczyk and Lawson, "Pocket-sized device for measuring . . . " British Medical Jornal, vol. 285, pp. 15–17, Jul. 3, 1982.
Saklad et al, "Pneumotachography:", Anesthesiology vol. 51, pp. 149–153; Aug. 1979.

Primary Examiner—Kyle L. Howell
Assistant Examiner—Kevin Pontius
Attorney, Agent, or Firm—Kane, Dalsimer, Sullivan, Kurucz, Levy, Eisele and Richard

[57] ABSTRACT

A self-contained portable spirometer includes a housing and an air tube with an orifice. Within the housing there is a transducer and microprocessor-based circuitry for generating standard exhaled air performance measurements such as forced expiration volume and peak expiratory flow rate, commonly referred to as $FEV_1$ and PFER. These measurements are displayed on a screen disposed on the housing. Since the air tube has a nonlinear response, two amplifier stages with different amplification are coupled between the transducer and the microprocessor. The microprocessor monitors the flow rate through the tube and selects the signal from either one or the other amplification stage depending on the flow through the tube. The microprocessor also monitors the flow to determine when no air is blown through the tube. In this latter case, the computer shuts the power to the analog circuitry to conserve power.

12 Claims, 8 Drawing Sheets

U.S. PATENT DOCUMENTS

| | | |
|---|---|---|
| 3,797,479 | 3/1974 | Graham . |
| 3,797,480 | 3/1974 | Williams .................................. 128/724 |
| 3,810,461 | 5/1974 | McCormick ........................ 128/728 |
| 3,818,901 | 6/1974 | Sanctuary et al. . |
| 3,822,699 | 7/1974 | Cleary .................................. 128/727 |
| 3,826,247 | 7/1974 | Ruskin et al. ........................ 128/727 |
| 3,848,583 | 11/1974 | Parr . |
| 3,862,628 | 1/1975 | Williams .................................. 128/727 |
| 3,871,364 | 3/1975 | Boehringer ........................ 128/727 |
| 3,894,536 | 7/1975 | Tysk .................................. 128/202.22 |
| 3,960,142 | 6/1976 | Elliott et al. . |
| 4,034,743 | 7/1977 | Greenwood et al. ................ 128/725 |
| 4,047,521 | 9/1977 | Kramer et al. . |
| 4,100,798 | 7/1978 | Nilsson et al. . |
| 4,122,842 | 10/1978 | Pikul . |
| 4,158,360 | 1/1979 | Adams .................................. 128/725 |
| 4,182,347 | 1/1980 | Russo .................................. 128/725 |
| 4,202,353 | 5/1980 | Hirsch et al. . |
| 4,206,754 | 6/1980 | Cox et al. ........................ 128/204.21 |
| 4,237,904 | 12/1980 | Franetzki ........................ 128/725 |
| 4,241,739 | 12/1980 | Elson . |
| 4,267,845 | 5/1981 | Robertson, Jr. et al. ............ 128/721 |
| 4,363,238 | 12/1982 | William .................................. 73/204 |
| 4,403,514 | 9/1983 | Osborn . |
| 4,406,291 | 9/1983 | Schwesinger . |
| 4,407,295 | 10/1983 | Steuer et al. . |
| 4,421,120 | 12/1983 | Edwards, Jr. et al. . |
| 4,425,805 | 1/1984 | Ogura et al. . |
| 4,444,201 | 4/1984 | Itoh .................................. 128/716 |
| 4,495,944 | 1/1985 | Brisson et al. . |
| 4,558,710 | 12/1985 | Eichler . |
| 4,638,812 | 1/1987 | Häkkinen ........................ 128/726 |
| 4,644,958 | 2/1987 | Brisson et al. . |
| 4,736,750 | 4/1988 | Valdespino et al. ................ 128/725 |
| 4,768,520 | 9/1988 | Varraux et al. . |
| 4,796,639 | 1/1989 | Snow et al. ........................ 128/725 |
| 4,807,641 | 2/1989 | Boehringer et al. ................ 128/725 |

OTHER PUBLICATIONS

Heinonen, E. "Spirometers: A Field Test Evaluation", Bull. Eur. Physiopathol. Respir. 1987 23.177–181.

Binder, R. C. "Fluid Mechanics" 5th Edition, Prentice Hall, 1959 pp. 236, 237.

Dalen, G. and Kjellman, B. "Valuation of Two Spirometers" Acta Paediatr Scand—71:253–256, 1982.

PERSONAL SPIROMETER

BACKGROUND OF THE INVENTION

1. Field of Invention

This invention pertains to an apparatus for automatic measure of the volume and flow rate of air exhaled by a person, and more particularly, to a personal spirometer small enough so that it can be carried unobtrusively in a pocket so that person can use it easily with maximum convenience and minimum embarrassment.

2. Description of the Prior Art

Spirometers are devices used to measure the volume and flow rate of air exhaled by a person. These measurements are important of general physiological studies and for diagnostic analysis of particular patients. For example, the effects of various medicines used to treat patients with pulmonary or asthmatic problems can be best analyzed by monitoring the volume and flow rate of air exhaled at regular intervals before and after the administration of medication.

In general, spirometers make their measurement by one of two means. One type collects the exhaled volume from the subject into a bellows or other container, the displacement of which corresponds to the volume of exhaled air. These devices are by their nature large to allow sufficient air collection volume and hence are not easily made portable. A second type measures the rate of air flow through a flow measurement device. Exhaled volume is derived by integration of the air flow rate over some period of time.

Until the present invention, spirometers were rather bulky and expensive devices found mostly in clinics and laboratories. Their operation required a trained technician. Furthermore, most such devices were complicated so that they could not be made small enough to be carried in a pocket. For example, there are several devices available in the market known as pneumotachs, such as the Fleisch Pneumotach. These devices depend on a laminar air flow past a resistance element. Such devices need additional means for insuring that the flow remains laminar even at high air velocities. Therefore, these type of devices are ir' rently complex and relatively large. Furthermore the resistance element frequently includes a screen disposed directly in the air path. This screen intercepts impurities which clog the screen and change the response of the device and in addition are unsanitary. The pneumotach also includes pressure measurement ports which frequently become occluded from moisture or impurities, thus adversely altering the accuracy of measurement.

OBJECTIVES AND SUMMARY OF THE INVENTION

An objective of the present invention is to provide an apparatus which may be used for an accurate and instantaneous measurement of exhaled air.

A further objective is to provide a self-contained apparatus which can be made small enough to fit in a person's pocket.

Another objective is to provide an apparatus which is simple enough to be used by the subject and is reliable without special care from the user.

Yet another objective is to provide an apparatus which can be adapted for data recording.

Other objectives and advantages of the invention shall become apparent from the following description of the invention. Briefly, an apparatus constructed in accordance with this invention includes a housing with an air tube in which turbulent flow is induced when a person blows air therethrough. The air tube is adapted for measurement of the flow rate of air exhaled therethrough. A pressure transducer within the housing senses a pressure differential created by said exhaled air and produces electrical signals indicative of said pressure differential. Signal processing circuitry within the housing processes these electrical signals to calculate the volume and rate of exhaled air and display the same on a display window. Preferably, the spirometer displays two parameters known as $FEV_1$ (the volume of air exhaled in one second in liters) and PEFR (peak expiratory flow rate in liters per second). Optionally the results of several measurements may be recorded in a memory for later down-loading to a data processing system.

An adaptive start algorithm is used to detect a true test, using a statistical approach rather than a preset threshold level. More particularly, the device calculates the average and the variance of a window formed of four consecutive samples and flow rate and volume calculations are started only if a progressive increase in the measurements is detected. This approach is found to provide good sensitivity and, at the same time, it is relatively immune to noise.

Furthermore, the spirometer takes advantage of the non-linear characteristics of the air tube to increase sensitivity without expensive high resolution A/D converters. Separate look-up tables for high and low flow rates are used to convert pressure differential samples into actual flow rates.

DETAILED DESCRIPTION OF THE INVENTION

Figure 2:
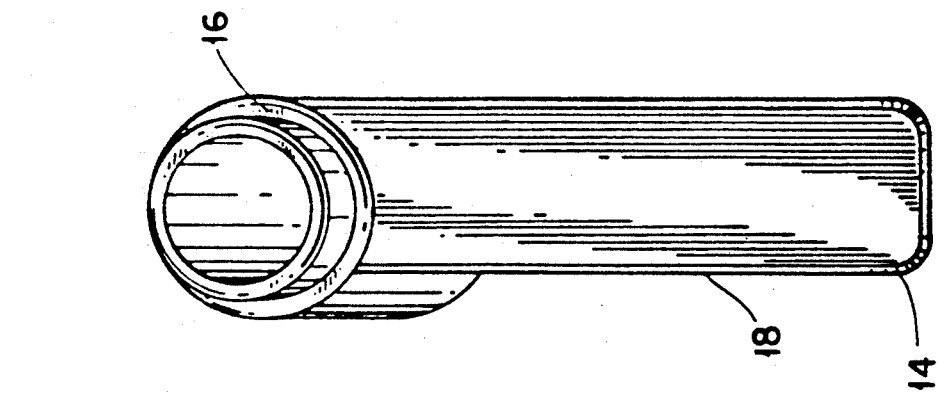
FIG. 2 shows a front view of the spirometer of FIG. 1.

Referring now to the drawings, a personal spirometer 10 constructed in accordance with this invention includes a housing 12 with a generally square section 14 and an air tube 16 disposed on one side of the section 14. The spirometer is sized and shaped so that it can fit in a pocket. Furthermore, the spirometer is shaped and sized so that it can be held comfortably in one hand while air is exhaled through it as described more fully below. The section 14 has a flat surface 18. A control panel 20 is imbedded in surface 18 and it includes a start button 22' and an LCD display screen 24. Air tube 16 has an annular mouth piece 26 at one end sized to fit in a person's mouth. A cylindrical hole 28 passes through the air tube 16. Hole 28 has a substantially constant diameter except at an annular wall 30. This annular wall 30 forms a sharp-edged orifice within hole 28. Two small openings 32, 34 are spaced on either side of the wall 30 and extend into section 14 for measuring the differential pressure within the air tube due to a flow of exhaled air.

Figure 4:
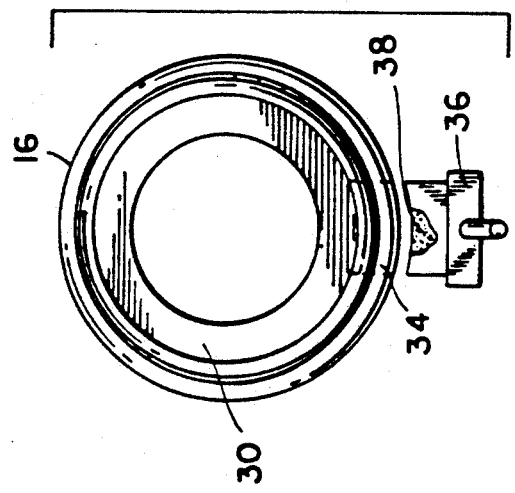
FIG. 4 shows an end view of the air tube of FIG. 3.

As shown more clearly in FIG. 4 each of the openings 32, 34 is provided with a plug 36, 36' (only one orifice being shown in FIG. 4). This plug holds a filter 38 at the interface with hole 28. The filter 38 may be made of a porous material which is permeable to air but impermeable to liquids. In this manner, saliva or other materials from the exhaled air of a person will be limited to the tube and will not contaminate the remainder of the spirometer 10. Furthermore since filter 38 is impermeable to water the spirometer may be immersed in or sprayed with water for cleaning and sanitary purposes. Filter 38 maybe made for example of a hydrophobic filter media such as a 1/16" thick hydrophobic polyethylene with a 10 micron pore size, and about 40% porosity.

Figure 5:
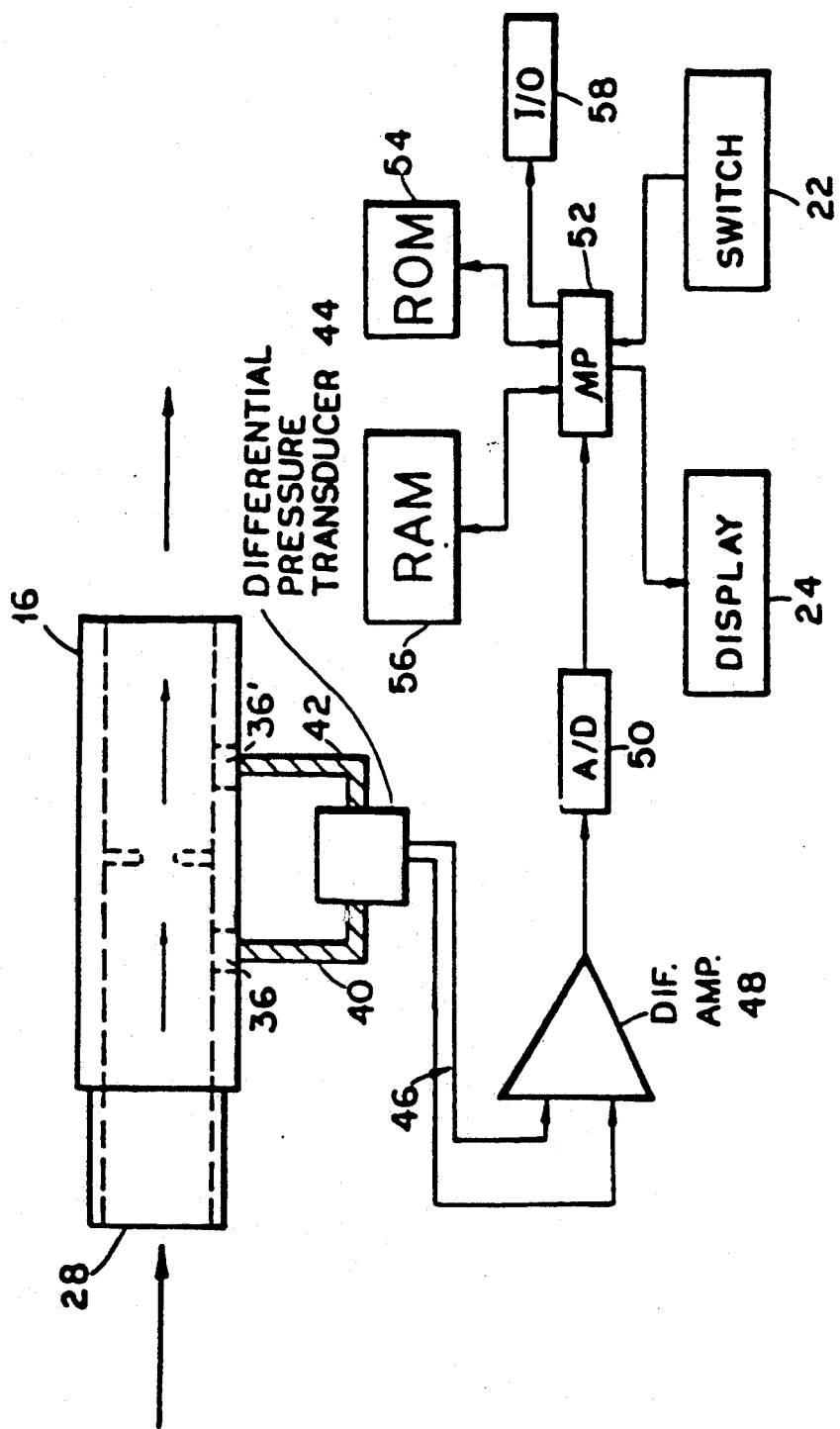
FIG. 5 shows somewhat schematic block diagram for the elements of the spirometer constructed in accordance with this invention.

As shown more clearly in FIG. 5, the plugs are connected by two tubes 40, 42 to a differential pressure transducer 44, which may be for example a MPX 2010D made by Motorola.

The transducer 44 generates an electrical signal on a pair of output wires 46, which signal is proportional to the differential pressure between tubes 40, 42. This signal is amplified by a differential amplifier stage 48 and fed into an analog-to-digital converter 50 which converts the amplifier output into digital signals. The converter output is fed to a microprocessor 52. The microprocessor 52 uses an algorithm stored in a ROM 54 to perform several calculations on the signal from converter 50, and to display the results (i.e. volume and rate of flow) on display 24. Switch 22 activated by button 22' initiates the operation of spirometer 10 through microprocessor 52. The results obtained during each measurement may be stored in a RAM 56 for future reference. An input/output port 58 may also be provided to allow for changing the programming of the microprocessor. Furthermore the microprocessor may be programmed so that on command it can down-load the results accumulated in RAM 56 through port 58 to a printer or a desk-top computer.

Figure 6A:
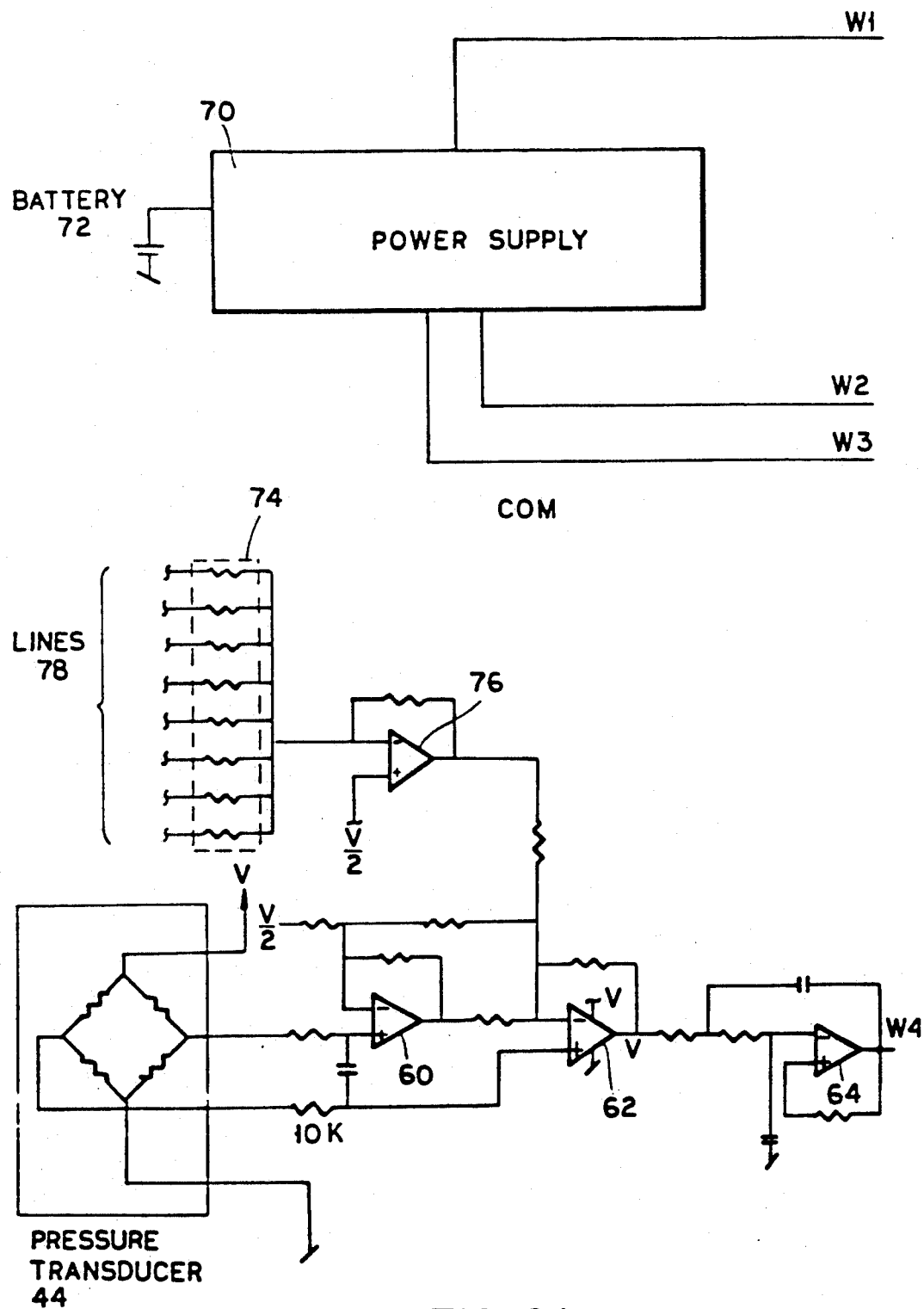
FIGS. 6A and 6B show an elementary wiring diagram of a preferred embodiment of the invention.
Figure 6B:
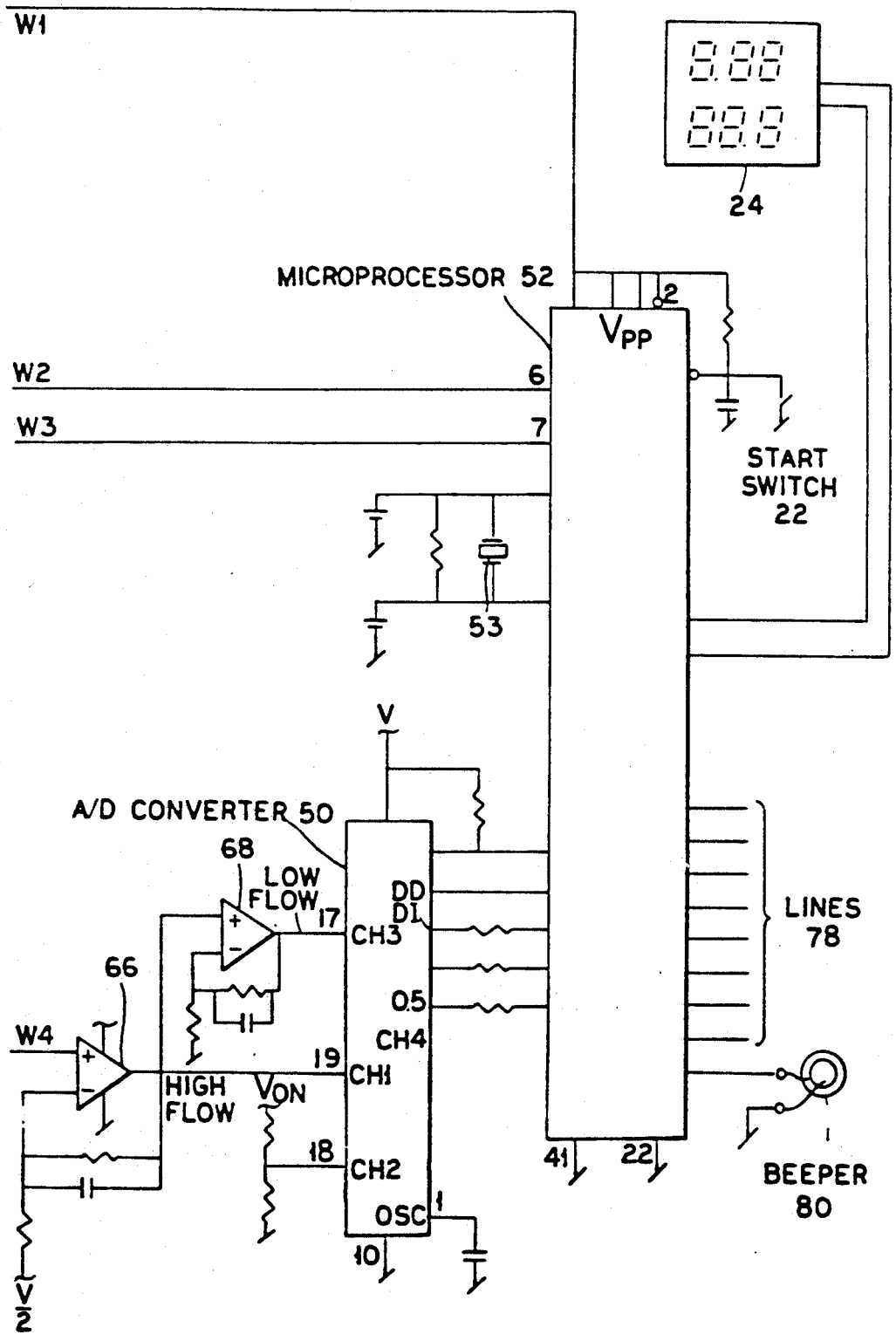

A preferred diagram for implementing the circuit shown in FIG. 5 is shown in FIGS. 6A and 6B. It should be understood that the various circuit elements (such as resistance and capacitance values) are shown in the Figures merely for illustrative purposes and do not limit the scope of this invention in any fashion.

In the embodiment of FIGS. 6A and 6B, differential air pressure in the air tube is sensed by the pressure transducer 44 schematically shown as a resistive bridge. The output of the transducer is processed by an amplifier analog circuit 48 consisting of amplifiers 60, 62, 64 and 66 which may be, for example, Motorola MC 34074 op amps. These amplifiers are used for a relatively high air flow. For low air flows a further amplifier 68 is also used. The outputs of these amplifiers 66, 68 are fed to a multiple channel A/D converter 50, which may be for example a 68HC68A2 manufactured by RCA Harris. The A/D converter 50 feeds its output to microprocessor 52 which may be for example a MC68HC804C4 made by Motorola. After performing the necessary calculations, the microprocessor 52 displays the results on the LCD screen 24. (Display screen 24 may also include LCD display drivers not shown in the Figures for the sake of convenience).

As shown in FIG. 6A, the circuit also includes a power supply 70 which provides the required power to the various circuit elements from a battery 72. The operation of the power supply is also controlled by wires W2, W3 by the microprocessor 52. More particularly, the analog section consisting of the amplifiers, the transducer and the digital-to-analog converter is turned on last (when measurements are started) and turned off first (when the measurements are completed) to conserve power. The power to the display screen is independently controlled. Preferably, the display is on whenever the microprocessor is on.

The spirometer 10 further includes a beeper 80 controlled by the microprocessor for generating audible signals for the user.

A further feature of the invention is a automatic offset compensation circuit consisting of plurality of resistors 74 and an amplifier 76. The resistors 74 are coupled to microprocessor 52 by a plurality of lines 78. This offset compensation circuit operates as follows. During the initialization of the spirometer (described more fully below), the microprocessor checks the output of the pressure transducer to insure that it essentially corresponds to no air flow. If the transducer output is non-zero (due for example to a temperature drift, a variation in the output of the power supply 70, the offset voltages of amplifiers 62, 64, 66, 68 and so on) the microprocessor 52 sends a compensating signal through lines 78 to resistors 74. Resistors 74 and amplifier 76 cooperate in effect to form a digital-to-analog converter used by the microprocessor 52 to produce a DC offset. This DC offset is added by amplifier 62 to the output of transducer 44. During the initialization period when no air is blown through the air tube, the microprocessor sequentially changes the signals on lines 78 until the offset signal from amplifier 76 compensates for the error signal from transducer 44.

OPERATION

The device requires no user adjustment or calibration. To make a measurement, the user pushes the START button 22'. This turns the unit on and initiates a self-test routine. During this self test, all segments on the liquid-crystal display (LCD) are turned on to allow the user to confirm proper operation of the unit. Upon completion of self-test (approximately 5 seconds), the display is blanked except for a READY annunciator: the unit beeps by activity beeper 80 and is now ready for a measurement. The user inhales as much as he can, places his lips around the mouthpiece 26, and blows as hard as possible. The device senses the start of exhalation, measures flow for one second, then displays performance signals such as the forced expiration volume and maximum rate of air flow for the person (commonly known as FEV; and PEFR respectively) measurements on display screen 24.

The parameter FEV; and the criteria for measuring this parameter is described in the Official Statement of American Thoracic Society, Medical Section of the American Lung Association —Standardization of Spirometry—1987 Update found in Respiratory Care, November '87, Vol. 32, No. 11, pgs. 1039-1060. The parameter PEFR is identical to the $FEF_{max}$ parameter in the same Statement.

The display will persist for 45 seconds, and then the unit will turn itself off, unless the START button 22' is pushed to initiate another measurement cycle. If no breath is detected within 15 seconds of the READY signal, the unit beeps twice and shuts itself off.

PRINCIPLE OF MEASUREMENT

The spirometer 10 determines the flow rate of air by measuring the differences in pressure developed across a restricting orifice. This pressure difference is related to the flow rate by a well-known equation based on Bernoulli's equation for non-compressible flow. (See for instance Binder, R. C., Fluid Mechanics, 5th Edition, Prentice Hall Inc., Englewood Cliffs, N.J., pgs. 236–237.) In the case of the sharp-edged orifice used in this device, the flow rate is equal to a coefficient (found empirically) multiplied by the square-root of the pressure difference measured between a point upstream of the orifice and a point downstream of the orifice. The value of the coefficient is predominantly determined by the physical design of the device, including the ratio of the area of the flow tube to the area of the orifice, the size of the orifice, and the location of the pressure measurement ports. Ideally, if these physical parameters were held constant, the pressure difference would be dependent only upon the flow rate and density of the fluid being measured. However, there is also some influence of Reynolds Number upon the value of the coefficient, which introduces an error if the coefficient is treated as a constant over a large range of flows.

The pressure difference across the orifice is a function of the square of the flow rate. Therefore, an orifice size must be chosen that does not offer excessive back-pressure to the highest flows to be measured, yet has an adequate, measurable pressure difference at low flow rates.

THEORY OF OPERATION

Figure 1:
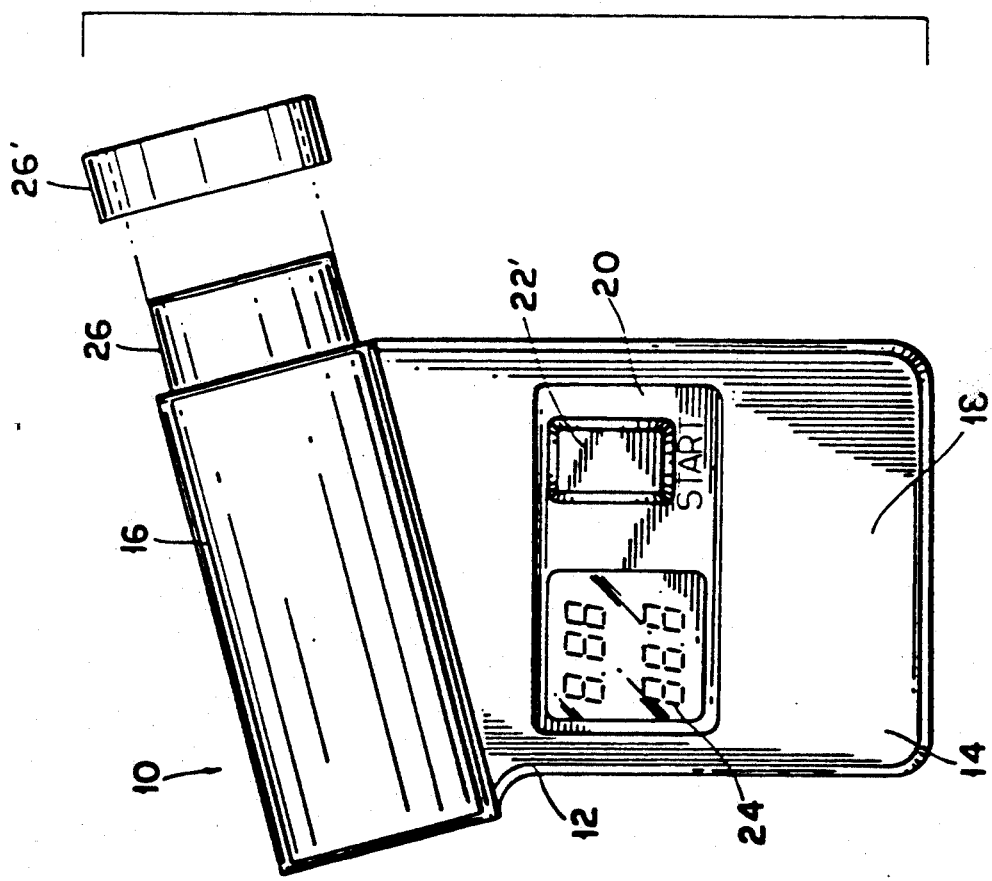
FIG. 1 shows a side view of a personal spirometer constructed in accordance with the invention.
Figure 3:
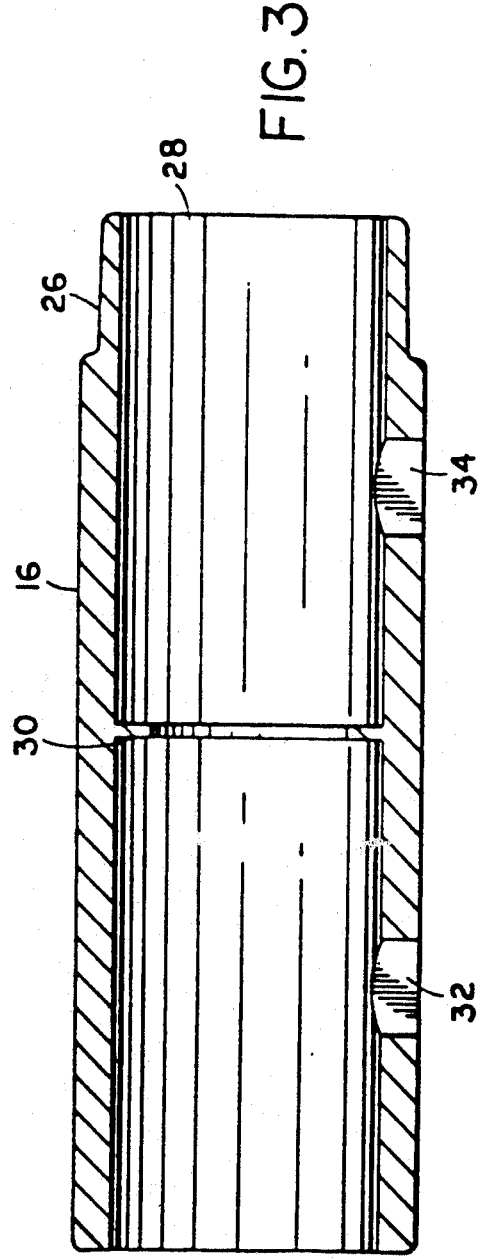
FIG. 3 shows a cross-sectional view of the air tube of FIGS. 1 and 3.

The air tube 16 contains the sharp-edged orifice (defined by wall 32) that provides a pressure difference which is approximately proportional to the flow rate squared. Preferably, the diameter is about 5/8" and tube 16 has a diameter of about 7/8". This size represents a reasonable compromise between back-pressure at higher flows and at low flows. The outside diameter of the tube 16 is approximately 1", and the length is approximately 3.5". Again, the dimensions represent a compromise; an attempt has been made to keep the overall size small enough to fit a pocket or handbag, yet large enough so that an extraneous mouthpiece is unnecessary. However, a tapered profile is provided on the inlet end of the tube so that a disposable mouthpiece may be added (26' in FIG. 1) if desired. The pressure ports are covered with a disk of hydrophobic filter material (as described above) inset flush with the floor of the tube. This material allows air and water vapor to pass freely, but blocks dirt and liquid. It is made of a 1/16" thick rigid plastic and is not easily damaged, allowing the interior of the tube to be cleaned with gently running water or wiped with a soft, lint-free cloth.

The pressure is transmitted via the 1/16" i.d. pipes 40, 42 to the solid-state, piezo-resistive, differential pressure transducer 44. This transducer is provided with a reduced amount of silicon isolation gel coating its diaphragm as compared with the standard transducers used for other measurements. This coating improves the transient response and reduces the sensitivity of the transducer to the position and motion of the spirometer. The differential pressure transducer provides an output signal proportional to the pressure difference between the two openings 32, 34.

The signal from the transducer is amplified and filtered by the 4-stage analog amplifier circuit shown in FIGS. 6A and 6B. Two outputs are produced by this amplifier circuit. The first circuit generated by amplifier 66 has a total gain of 808. The second circuit generated by amplifier 68 has a total gain of 3,232.

The offset voltage of this circuit is adjusted to 300 $+/-50$ mV at the first output as described above.

Two filter stages (including amplifiers 64, 66) are included in the analog amplifier circuitry providing a low-pass transfer function with a cut-off frequency of 10 hz. The first and second outputs from the analog circuitry are fed to two channels marked CH1, CH3 of the 10-bit A/D converter 50. A signal proportional to th voltage of battery 72 is fed to channel CH2 on the A/D converter 50.

The microprocessor controls all aspects of device function. It is able to independently control power to the display, the pressure transducer and analog circuitry, and itself. Timing pulses are provided by a 3.59 MHz crystal 53. The microprocessor receives the digital values representing pressure, does all necessary calculations, and generates the codes for the liquid-crystal display circuitry.

The liquid-crystal display shows the measured values for $FEV_1$ and Peak Expiratory Flow Rate (PEFR). It also includes a BATTERY annunciator to indicate when the battery needs replacement and a READY annunciator to indicate when the device is ready to make a measurement.

MEASUREMENT SEQUENCE

Figure 7A:
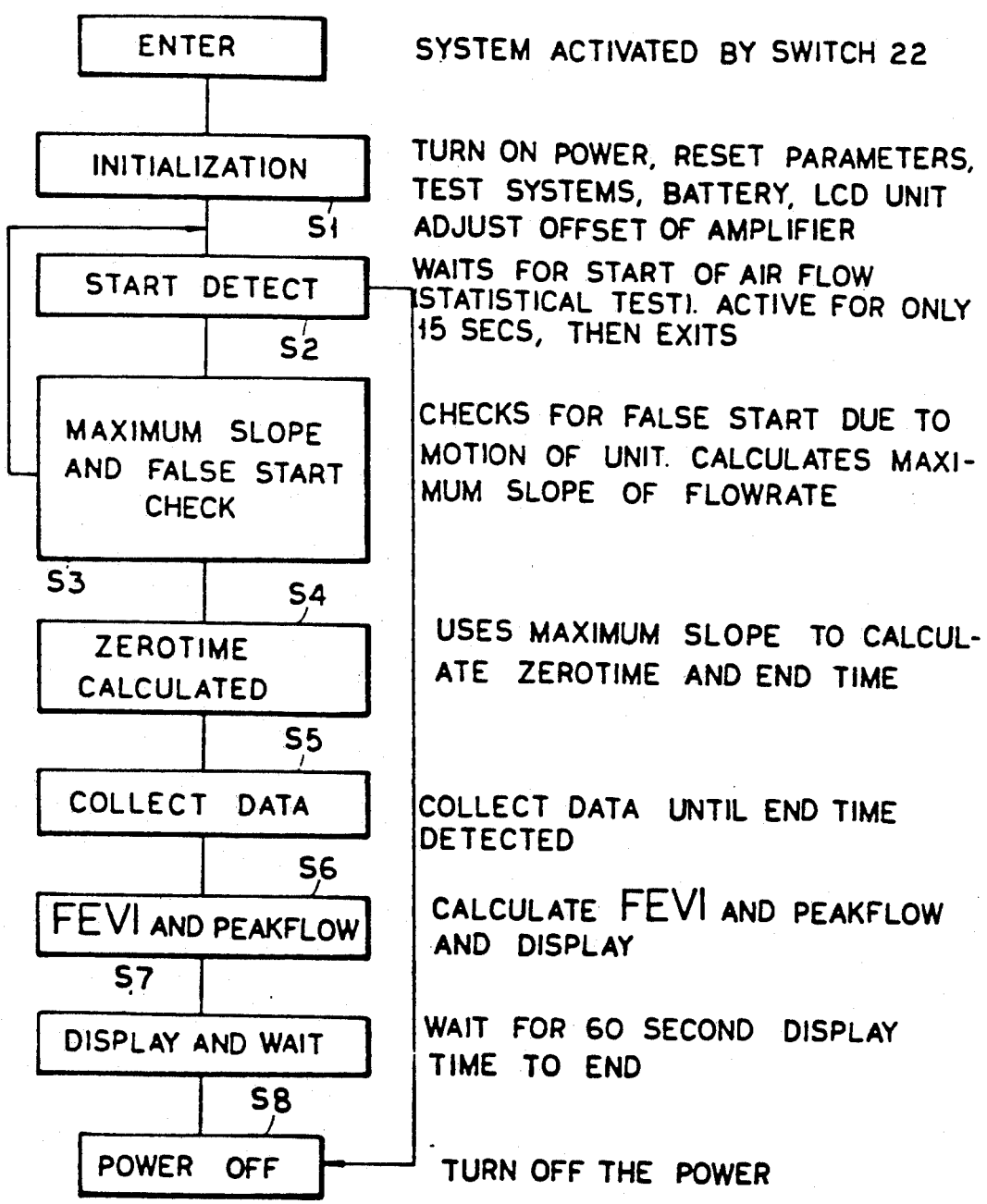
FIGS. 7A, 7B and 7C show flow charts for the operation of the microprocessor for the spirometer.
Figure 7B:
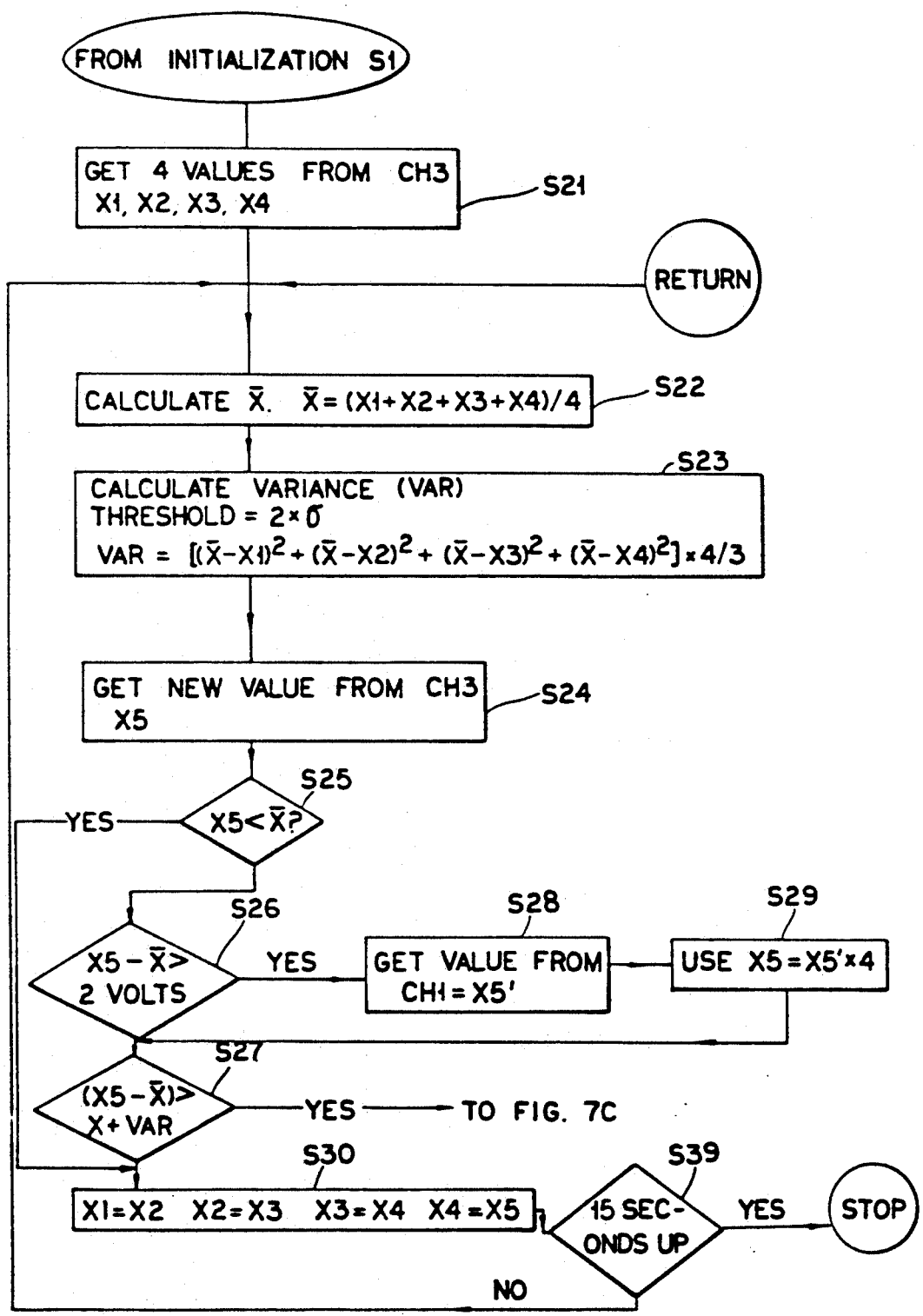
Figure 7C:
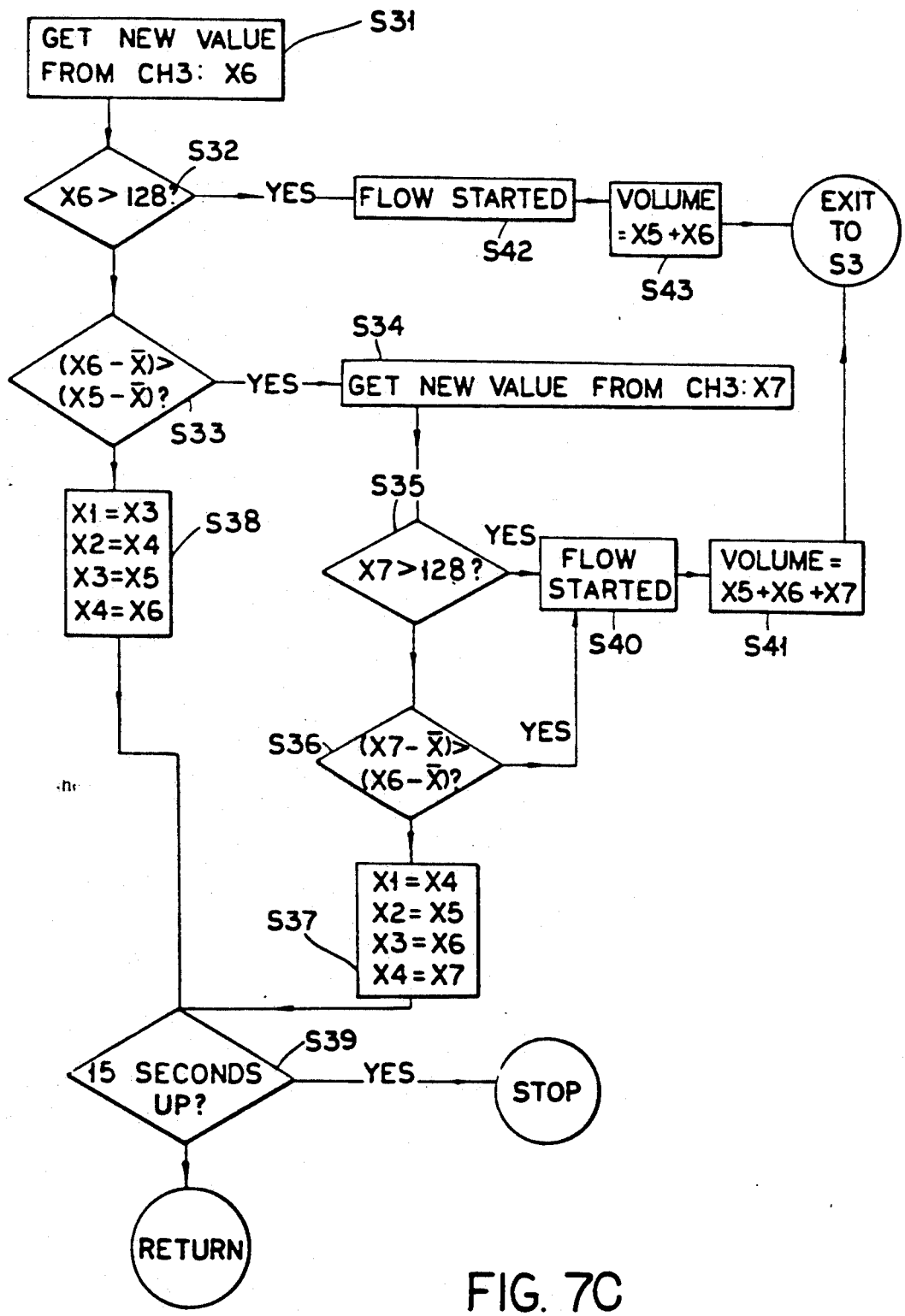

The sequence of operation for the spirometer is now described in conjunction with the flow charts of FIGS. 7A, 7B and 7C. Details of the operations are found in the program listing attached hereto. When the start switch is depressed, the microprocessor 52 is reset and loads its program, which is stored in its Read-Only Memory (ROM) 54. It begins by running a self-test and initialization routine step S1 which checks for internal consistency. It also measures the voltage of battery 72 through input channel CH2 of the A/D converter 52. If the voltage is below a lower limit such that an accurate measurement cannot be made, the microprocessor will not continue. If the voltage is low, but does not exceed this operational limit, the BATTERY annunciator on the LCD is turned on and will not extinguish until the unit turns itself off. If the internal checkout is completed without error, the microprocessor then turns on all segments of the display to allow the user to see if any segments are non-functional. Next, it starts sampling the input on channel CH1 of the A/D converter so as to decide which bits of the digital-to-analog converter (I/O lines 78) to turn on or off and to adjust the offset voltage at channel CH1 to $300+/-50$ mV. This sequence takes about 2 seconds.

At the end of offset adjustment, the display is blanked (except for the battery annunciator, if voltage is low) and then analog circuitry is allowed to stabilize. The microprocessor in step S2 begins to sample both CH1 and CH3 inputs of the A/D converter signals at a rate of about 100 Hz and fills its history array as described below.

The subroutines for step S2 are shown in FIGS. 7B and 7C. The unit continues to sample both the CH1 and CH4 channels at 100 Hz each. It continuously calculates the average and variance of the past four measurements X1, X2, X3 and X4 from the CH3 channel (Steps S21, 22 and 23). It then compares the next sample (X5) to this average and variance in Steps S24, S26. If the current value is higher than the average by more than 2 standard deviations, the unit branches to a start detection routine (Step 27). If the value is more than 2 volts higher than the average, the microprocessor 52 switches over to the CH1 channel (Step 28) and scales the reading (Step 29). If the current value is lower than the average or is less than 2 standard deviations higher than the average, the current value becomes the new 4th sample in the average and variance calculation and the loop continues (Steps 22, 30, 39). This loop will continue for a maximum of 15 seconds. If no start is detected (as described below) in this time, the unit will beep twice and turn itself off in step S8.

If the current sample value is high enough to cause branching to the start detection routine, the old average and variance are saved. In Steps 31, 32 the next sample is now checked to see if it is also above a threshold level 128 (Step 32) or the 2 standard deviation threshold (using either the CH3 or CH1 channel, depending on how large the input on channel CH3 is), and also to see if it is higher than the previous sample (Step 33). If both of these conditions are met, a third sample is obtained and checked in the same way (Step 34). (It must be larger than second sample.) If either the second or third sample fails either test, the average and variance are updated using the new sample values and the program returns to the loop above (Steps 35, 36, 37, 38, 39). If three samples in a row are larger than the threshold value 128 or the average plus 2 standard deviations, and each is larger than the one preceding it, then start is detected (Steps 40, 41, 42, 43). The saved average is stored as the offset to be subtracted from all samples and the 3 samples are converted to flow values and summed as the first three volume increments (Step 41). The actual conversion from the measurement pressure differential samples to volumes is accomplished by using two look-up tables stored in ROM 54. One look-up table correlates samples from the low flow channel CH3 (i.e. 0-2 volts) while the second look-up table correlates the samples from the high flow rate channel CH1 (i.e. 0-4 volts). The values on these look-up tables are determined empirically. As previously mentioned, the orifice used to measure flow rate has a non-linear response, i.e. the pressure differential across the openings 32, 34 due to turbulent flow is non-linear. The present spirometer takes advantage of this non-lineality by separating the pressure differential samples into two ranges based on the flow rate, and then using a look-up table for each. By switching gains, the microprocessor has expanded resolution at low flows. This would be analogous to an equivalent linear range of 16 volts at 10 bits of resolution, or 4 volts at 12 bits of resolution. This feature is made possible by the non-linear characteristic of the orifice. To conserve microprocessor memory space, rather than store a value for every possible A/D code, the microprocessor extrapolates between the two closest stored values. Enough samples are stored to keep the extrapolation error small. In this manner, a less-discriminating (having lower resolution) A/D converter can be used without sacrificing accuracy and sensitivity.

Once start is detected and integration of flow values has begun, the unit begins to look for the maximum slope of the volume curve (step S3). If the slope determined by several consecutive samples is low or negative, the whole measurement is reported as a false start. The maximum positive slope is determined over seven flow samples and, when found, is back extrapolated to determine the start of the first second timing for FEV; determination in accordance with the standards set by the American Thoracic Society identified above (step S4). Meantime, each 10 msec. the CH1 and CH3 channels are sampled (step S5). If the CH3 output is less than 2 volts above the offset, it is converted to flow and summed. If the CH3 input is more than 2 volts, the input from channel CH1 is used instead. The unit also looks for, and stores the highest flow sample (step 6).

When the $FEV_1$ timing has been determined, flow samples have been collected and integrated as volume, and the peak flow value has been stored, the unit displays the measured $FEV_1$ and PEFR (step S7) and it turns off the analog circuitry to save battery life. The display is maintained for 45 seconds (or until the START button 22' is pushed to initiate another measurement cycle). After 45 seconds, the microprocessor powers down (step S8) to an idle mode.

The operation and circuitry described above and in FIGS. 6A, 6B and 7 pertain to a basic spirometer. For more advanced modes additional features may be incorporated mostly by modifying the programming of microprocessor 52. For example, before the unit goes into the idle mode, each measurement may be stored into RAM 54 with a time stamp and/or date stamp indicating the time and day on which the measurements were made. The measurements are then recalled and reviewed on the display screen sequentially by activating switch 22. As an incentive, the instantaneous flow measurements could be displayed as the person blows through air tube 26, and when certain mile stones are reached, the beeper could be sounded.

Obviously numerous other modifications can be made to the invention without departing from its scope as defined in the appended claims.

We claim:

1. A portable spirometer comprising:
   a housing;
   an air tube coupled to said housing and including a substantially linear air passage with a reduced diameter orifice for generating a turbulence in the air passage;
   pressure sensing means for sensing a differential pressure across said orifice when a person exhales through said air tube;
   filter means disposed at an interface between said tube and said pressure sensing means for protecting said pressure sensing means, said filter means being made of a material permeable to gases and impermeable to liquids;
   electronic circuitry means disposed in said housing and coupled to said pressure sensing means for generating electric input signals corresponding to said differential pressure, said electronic circuitry means including calculating means for calculating performance signals from said electric input signals; and
   display means for displaying said performance signals.

2. The spirometer of claim 1 wherein said pressure sensing means includes access holes disposed in said air tube and spaced from said orifice, and transducer means coupled to said access holes for generating a transducer output corresponding to said differential pressure.

3. The spirometer of claim 1 further comprising power supply means disposed in said housing for supplying said circuitry means with electrical power, said circuitry means deactivating said power supply means when said spirometer is in an idle mode.

4. The spirometer of claim 3 wherein said electronic circuitry means includes analog circuit means and digital circuit means, and wherein said power supply means provides power to said analog circuit means when said spirometer is not in said idle mode.

5. The spirometer of claim 3 wherein said power supply means includes a battery to make said spirometer self-contained.

6. The spirometer of claim 1 further comprising voltage offset compensation means for offsetting voltage offsets in said circuitry means.

7. The spirometer of claim 6 wherein said voltage offset compensation means includes digital-to-analog convertor means for receiving an error signal from said means corresponding to said voltage offset and said converter means generating a convertor output.

8. The portable spirometer of claim 1 wherein said electronic circuitry means includes first amplifier means for amplifying said electric input signals by a first factor to generate a first amplified output, second amplifier means for amplifying said electric input signals by a second factor to generate a second amplified output, and microprocessor means being coupled to first and second amplified output, said microprocessor means being programmed to select one of said one of said first and second amplified outputs to calculate said performance signals.

9. The portable spirometer of claim 8 wherein said electronic circuitry means further includes analog-to-digital converter means for converting said first and second amplified output for said microprocessor means.

10. The portable spirometer of claim 8 wherein said air passage has a non-linear response to air flow, and wherein said microprocessor means includes select means which selects said first amplified output in response to a first air flow below a threshold level, and wherein said select means selects said second amplified output in response to a high air flow above said threshold level.

11. The portable spirometer of claim 8 wherein said microprocessor means includes sampling means which samples the air flow through said air passage and which calculates a running average signal.

12. The spirometer of claim 11 wherein said microprocessor means includes monitoring means which monitors said average signal to discriminate a test from noise.

* * * * *

UNITED STATES PATENT AND TRADEMARK OFFICE
CERTIFICATE OF CORRECTION

PATENT NO. : 5,137,026
DATED : August 11, 1992
INVENTOR(S) : Charles K. Waterson and Frederick A. Ebeling It is certified that error appears in the above-identified patent and that said Letters Patent is hereby corrected as shown below:

Col. 2, line 12; "FEV" should read -- $FEV_1$ --

Col. 4, line 54; "FEV" should read -- $FEV_1$ --

Col. 4, line 56; "FEV" should read -- $FEV_1$ --

Col. 8, line 3; "FEV" should read -- $FEV_1$ --

Col. 9, line 19; before the word "means" insert the word
-- microprocessor --

Signed and Sealed this

Seventh Day of September, 1993

*Attest:*

BRUCE LEHMAN

*Attesting Officer*   Commissioner of Patents and Trademarks